United States Patent [19]

Alul

[11] Patent Number: 5,532,130
[45] Date of Patent: Jul. 2, 1996

[54] METHODS AND COMPOSITIONS FOR SEQUENCE-SPECIFIC HYBRIDIZATION OF RNA BY 2'-5' OLIGONUCLEOTIDES

[75] Inventor: Rushdi Alul, Columbia, Md.

[73] Assignee: Dyad Pharmaceutical Corporation, Columbia, Md.

[21] Appl. No.: 93,757

[22] Filed: Jul. 20, 1993

[51] Int. Cl.$^6$ .................................................. C12Q 1/68
[52] U.S. Cl. .......................... 435/6; 536/23.1; 536/24.3; 536/25.2; 935/78
[58] Field of Search .............................. 514/44; 536/23.1, 536/24.5, 25.2, 24.3; 935/78; 435/6

[56] References Cited

U.S. PATENT DOCUMENTS 4,464,359  8/1984  Suhadolnik et al. .................. 514/47
4,924,624  5/1990  Suhadolnik .......................... 47/58

FOREIGN PATENT DOCUMENTS 9111535  8/1991  WIPO.

OTHER PUBLICATIONS

Damha, et al., *Nucleic Acids Research*, p. 290 Symp. Ser. No. 24, 1991.
Giannaris, et al., *Nucleic Acids Research*, 4742–49, 21:20, (1993).
Uhlmann et al (1990) Chemical Reviews 90(4): 543–584.
Dougherty et al (1992) J Am Chem Soc 114(15): 6254–5.

*Primary Examiner*—Jacqueline M. Stone
*Assistant Examiner*—Bruce R. Campell
*Attorney, Agent, or Firm*—Max Stul Oppenheimer

[57] ABSTRACT

(2'–5') linked 3'-Deoxyoligodeoxynucleotides have been synthesized on a solid support via standard cyanoethyl phosphoramidite chemistry. This simple change in the oligonucleotide bond connectivity leads to unique properties. Thus (2'–5') 3'-deoxyoligodeoxynucleotides hybridize selectively to single stranded RNA but not DNA. The (2'–5') linkages confer greater resistance to exo- and endonucleolytic degradation compared to (3'–5') -linked oligomers. In addition, (2'–5') linked 3'-deoxyoligodeoxynucleotides support RNase-H activity. The nucleic acid selectivity of (2'–5')oligo-3'0-deoxynucleotides may represent an important design feature to improve the efficacy of antisense oligonucleotides.

14 Claims, 1 Drawing Sheet

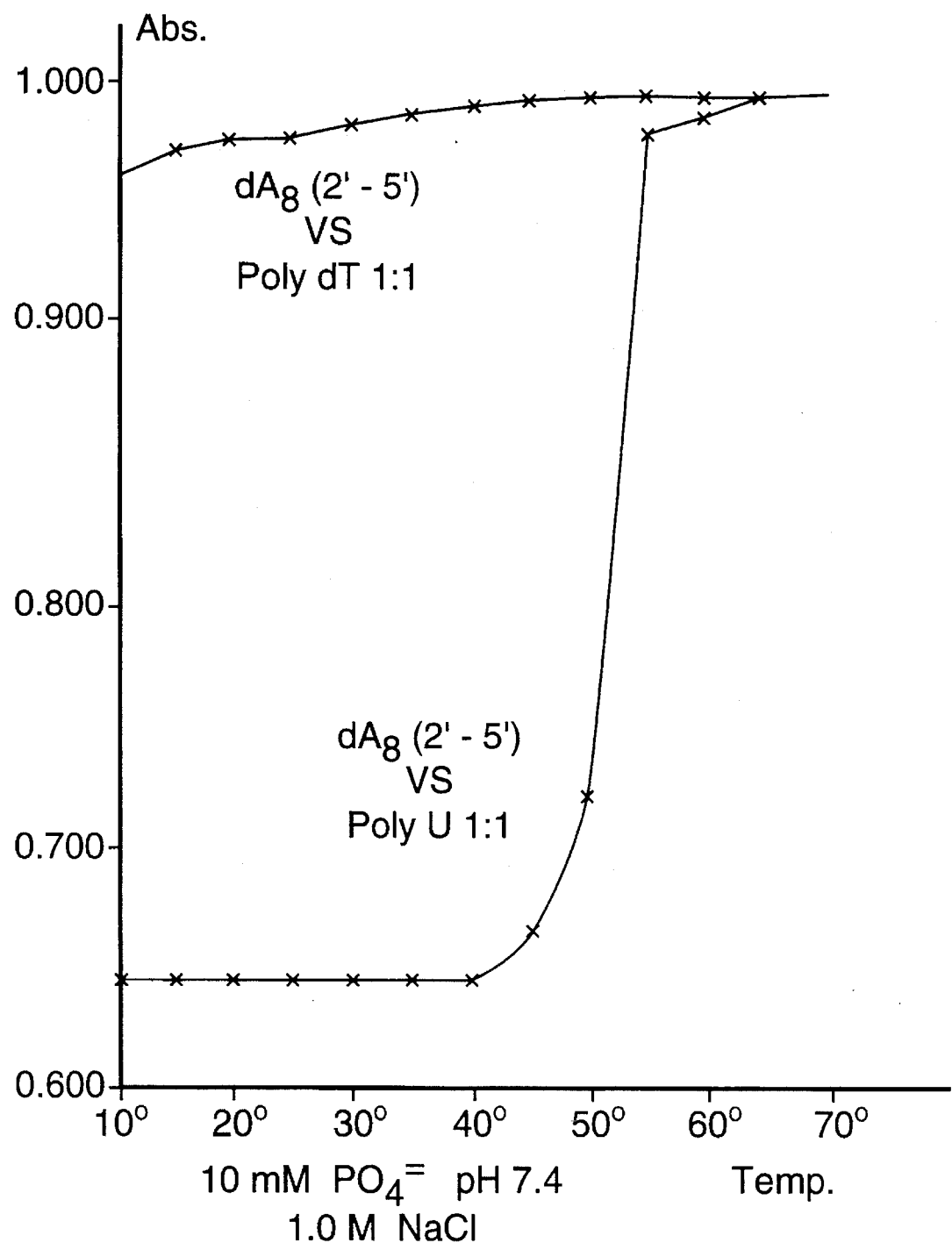

METHODS AND COMPOSITIONS FOR SEQUENCE-SPECIFIC HYBRIDIZATION OF RNA BY 2'-5' OLIGONUCLEOTIDES

FIELD OF THE INVENTION

It is the primary objective of this invention to provide 2'–5' oligonucleotides as therapeutic agents to selectively block gene expression in a sequence-specific manner. In particular, this invention is directed to the selective inhibition of protein translation via an antisense strategy using 2'–5' oligonucleotides i.e. nucleotides connected by 2'–5' intersugar linkages. More particularly this invention relates to the use of antisense oligonucleotides having 2'–5' internucleotide linkages to hybridize to complementary human mRNAs or pre-mRNAs. More particularly this invention relates to the use of (2'–5')oligo-3'-deoxynucleotides containing a natural phosphodiester backbone to selectively hybridize complementary RNA. This invention further relates to the synthesis of (2'–5')oligo-3'-deoxynucleotides via a solid-phase phosphoramidite approach. This invention also relates to the use of 2'–5' oligonucleotides to hybridize to a complementary DNA duplex to form a triple helix and thereby block transcription.

BACKGROUND OF THE INVENTION

Sequence specific interactions between nucleic acids by Watson-Crick base pairing, or between nucleic acids and proteins proceed by well-defined recognition rules which govern all steps of gene expression. In principle, specific interference with any such event would provide a means to control cellular or viral gene expression. The antisense strategy has been used in a pharmacological manner to block the expression of various genes (for reviews see: (i) Uhlman, E.; Peyman, A. *Chem. Rev.* 1990, 90, 543. (ii) Stein, C. A.; Cohen, J. A. *Cancer Res.* 1988, 48, 2659. (iii) Matteucci, M. D.; Bischofberger, N. *Annu. Rep. Med. Chem.* 1991, 26, 287. (iv) Miller, P. S.; Ts'o, P. O. P. *Annu. Rep. Med. Chem.* 1988, 23, 295. (v) Neckers, L.; Whitesell, L.; Rosolen, A; Geselowitz, D. A. *Critical Revs. Oncogenesis* 1992, 3, 175. (vi) *Gene Regulation: Biology of Antisense RNA and DNA*, Volume 1, Erickson, R. P.; Izant, J. G., Eds.; Raven Press: New York 1992). Antisense oligonucleotides are short single-stranded DNA or RNA fragments whose nucleotide sequence is complementary to a specific sequence within the target mRNA. The antisense oligonucleotide hybridizes to the mRNA which thereby inhibits gene expression by possibly blocking processing, transport, or translation of the sense mRNA. The inhibition of translation observed may also be due to cleavage of the mRNA by ribonuclease H (RNase H), an enzyme found in the nuclei of mammalian cells that is able to hydrolyze the RNA strand of an RNA-DNA hybrid. Endogenous RNase H-like activity may play a role in the specific inhibiting properties of antisense oligonucleotides observed in cultured cells.

Examples of the success of the antisense strategy using oligonucleotides include inhibition of Herpes simplex virus replication (Kulka, M.; Smith, C. C.; Aurelian, L.; Fishelevich, R.; Meade, K.; Miller, P.; Ts'o, P. O. P. *Proc. Natl. Acad. Sci. USA* 1989, 86, 6868) and blocking viral protein synthesis of HIV-1 (Agrawal, S.; Ikeuchi, T.; Sun, D.; Sarin, P. S.; Konepka, A.; Maizel, T.; Zamecnik, P. C. *Proc. Natl. Acad. Sci. USA* 1989, 86, 7790). Antisense oligonucleotides have also been shown to inhibit the expression of specific oncogenes in cell culture, such as c-myc (Wickstrom, E. L.; Bacon, T. A.; Gonzalez, A.; Freeman, D. L.; Lyman, G. H.; Wickstrom, E. *Proc. Natl. Acad. Sci. USA* 1988, 85, 1028) and c-myb (Gewirtz, A. M.; Calabretta, B. *Science* 1988, 242, 1303).

The goal in the development of antisense oligonucleotides is to inhibit specific gene expression in intact cells. The desired properties of antisense oligonucleotide and oligodeoxynucleotides includes stability against nucleases, membrane permeability and selective inhibition of gene expression. Unmodified phosphodiester antisense oligodeoxynucleotides and antisense RNA have been shown to inhibit translation of targeted mRNA but are susceptible to rapid degradation by nucleases within the cells as well as in mammalian sera. Therefore, much effort has been made to synthesize oligonucleotide analogs with modified internucleotide linkages e.g., phosphorothioate, (Eckstein, F.; *Annu. Rev. Biochem.* 1985, 54, 367) methylphosphonate (Ts'o, P. O. P.; Miller, P. S.; Aurelian, L.; Blake, K. R.; Murakami, A.; Agris, C.; Blake, K. R.; Lin, S. -B.; Lee, B. L.; Smith, C. C. *Ann. N.Y. Acad. Sci.* 1988, 507, 220) phosphorodithioate, (Brill, W. K. D.; Tang, J. -Y.; Ma, Y. -X.; Caruthers, M. H. *J. Am. Chem. Soc.* 1989, 111, 2321) ethylphosphotriester, (Miller, P. S.; Chandrasegaran, S.; Dow, D. L.; Pulford, S. M.; Kan, L. S. *Biochemistry* 1982, 21, 5468) and phosphoramidate (Froehler, B.; Ng, P.; Matteucci, M. *Nucleic Acids Res.* 1988, 16, 4831). The majority of the modifications are directed primarily towards the sugar-phosphate backbone and usually involve a minimal change of ligands around the phosphorous atom to prevent distortion in the geometry of the internucleotide bond and thereby maintain fidelity of oligomer binding while enhancing stability and nuclease resistance. There is as yet no universally applicable oligonucleotide structure to serve as an antisense effector. Unmodified phosphodiester oligodeoxynucleotides offer the advantages of good solubility, efficient and stable hybridization and activation of RNase H, but suffer from poor biological stability and poor cellular uptake. Methylphosphonate oligonucleotide analogs are poorly soluble and are unable to direct cleavage of RNA by RNase H. Phosphorothioates are able to survive longer than unmodified oligonucleotides in cells and media due to their nuclease resistance, however, they enter cells more slowly, possibly a result of stronger binding to one or more cell-surface receptors or other proteins (Loke, S. L.; Stein, C. A.; Zhang, X. H.; Mori, K.; Nakanishi, M.; Subasinghe, C.; Cohen, J. S.; Neckers, L. M. *Proc. Natl. Acad. Sci. USA* 1989, 86, 3474). Phosphorothioates also suffer from the disadvantages of toxicity and non-specific inhibition of protein and DNA synthesis at concentrations which are near those required for sequence-specific effects. Phosphorothioate and methylphosphonate backbone-modified oligodeoxynucleotides exist as diasteromeric mixtures and form less stable hybrids than normal phosphodiester oligonucleotides (Freier, S. M.; Lima, W. F.; Sanghvi, Y. S.; Vickers, T.; Zounes, M.; Cook, P. D.; Ecker, D. J. in *Gene Regulation: Biology of Antisense RNA and DNA*, Volume 1, pp.95–107; Erikson, R. P.; Izant, J. G., Eds.; Raven Press: New York 1992) (Miller, P. S.; Yano, J.; Yano, E.; Carroll, C.; Jayaraman, K.; Ts'o, P. O. P. *Biochemistry* 1979, 18, 5134). Chirality may also be important in the case of phosphorothioates in directing RNase H activation of the phosphorothioate oligodeoxynucleotide-RNA heteroduplex. Agrawal has reported that phosphodiester-linked oligodeoxynucleotides are more efficient than the corresponding phosphorothioate analogs with respect to human RNase H activity (Agrawal, S.; Mayrand, S. H.; Zamecnik, P.; Pederson, T. *Proc. Natl. Acad. Sci. USA* 1990, 87, 1401). The ability to serve as a template for RNase H may have therapeutic value by mediating, or at least enhancing the antisense effect relative to oligonucleotides that are unable to activate RNase H. However the exact role of an RNase H activity in intact cells remains to be ascertained.

The problems arising for example, from chirality, steric hindrance, or hydrophobicity as well as the potential risk of toxicity and antigenicity in vivo, prompted us to consider oligodeoxynucleotides which are constitutional isomers of biological DNA differing only in bond connectivity. One possible approach to modifying an oligonucleotide to generate a constitutional DNA isomer involves the alteration of the sugar moiety. The reversion of the configuration of the 1' carbon atom of the sugar residue results in α-oligonucleotide analogs (Morvan, F.; Rayner, B.; Imbach, J. -L.; Chang, D. K.; Lown, J. W. *Nucleic Acids Res.* 1986, 14, 5019) (Morvan, F.; Rayner, B.; Imbach, J. -L.; Lee, M.; Hartley, J. A.; Chang, D. K.; Lown, J. W. *Nucleic Acids Res.* 1987, 15, 7027) (Imbach, J. -L.; Rayner, B.; Morvan, F. *Nucleosides & Nucleotides* 1989, 8, 627). Oligo-α-deoxynucleotides are nuclease resistant and form stable double helices with complementary DNA or RNA sequences (Gagnor, C.; Bertrand, J. R.; Theret, S.; Lemaitre, M.; Morvan, F.; Rayner, B.; Malvey, C.; Lebleu, B.; Imbach, J. -L.; Paoletti, C. *Nucleic Acids Res.* 1987, 15, 10419) (Cazenave, C.; Chevrier, M; Thuong, N. T.; Hélène, C. *Nucleic Acids Res.* 1987, 15, 10507). They are capable of antisense inhibition of β-globin mRNA translation via an RNase H independent mechanism (Boiziau, C.; Kurfurst, R.; Cazenave, C.; Roig, V.; Thuong, N. T. *Nucleic Acids Res.* 1991, 19, 1113). Similarly, Beaucage has recently reported that alternating α,β-oligothymidylates with alternating (3'–5')- and (5'—5')-internucleotide phosphodiester linkages exhibit enhanced nuclease resistance and hybridize with satisfactory affinity to complementary DNA and RNA (Koga, M.; Moore, M. F.; Beaucage, S. L. *J. Org. Chem.* 1991, 12, 3757).

In some instances substitution of 2'-deoxy-β-D-ribofuranose by an isomeric sugar residue generates an oligodeoxynucleotide that exhibits selective hybridization to DNA and RNA complements. A pentadecanucleotide prepared from 1-α-D-arabinofuranosylthymine hybridizes with some selectivtity to complementary RNA rather than DNA (Adams, A. D.; Petrie, C. R.; Meyer, R. B. *Nucleic Acids Res.* 1991, 19, 3647). Another sugar modification which generates a constitutional DNA isomer is the replacement of the 2'-deoxy-D-ribose backbone by 2'-deoxy-L-erythro-pentose to give enantio-DNA. Enantio-DNA (L-dA$_6$) has been shown to be resistant to bovine spleen phosphodiesterase and binds complementary RNA preferentially to complementary DNA (Shizuyoshi, F.; Shudo, K. *J. Am. Chem. Soc.* 1990, 112, 7436).

The 2'–5'internucleotide linkages of oligoadenylates (2'–5')A$_n$, represent unique examples of naturally occurring constitutional RNA isomers. The (2'–5')A$_n$ oligomers have been detected in a variety of cells and tissues including L1210 cells and human lymphocyctes (Cailla, H.; LeBorne De Kaouel, C.; Roux, D.; Delage, M.; Marti, *J. Proc. Natl. Acad. Sci. USA* 1982, 79, 4742). The (2'–5')A$_n$ has been suspected to be involved in regulation of cell growth and differentiation and in the antiviral mechanism of interferon (Wells, M.; Mallucci, L. *Exp. Cell Res.* 1985, 159, 27). In the (2'–5')A pathway interferon and double-stranded RNA activate an enzyme, (2'–5')-oligoadenylate synthetase, to catalyze the formation of oligoadenylates from ATP linked 2'–5' rather than by the usual 3'–5' phosphodiester bonds. The oligoadenylates vary in length from two to fifteen residues. The di-, tri- and tetraadenylates are the most abundant and the amounts of larger oligoadenylates diminish with increasing chain lengths (Samanta, H.; Dougherty, J. P.; Lengyel, P. *J. Biol. Chem.* 1980, 255, 9807). The (2'–5')A$_n$ subsequently binds and activates an endoribonuclease (RNase L) which is responsible for the nonspecific cleavage of messenger and ribosomal RNAs and thereby inhibits protein synthesis in intact cell systems (Farrell, P. J.; Sen, G. G.; Dubois, M. F.; Ratner, L.; Slattery, R. E.; Lengyel, P. *Proc. Natl. Acad. Sci. USA* 1978, 75, 5893). Double-stranded RNA is not cleaved during the process (Ratner, L.; Sen, G. C.; Brown, G. E.; Lebleu, B.; Kawakita, M.;Cabrer, B.; Slattery, E.; Lengyel, P. *Eur. J. Biochem.* 1977, 79, 565).

The biological activity of (2'–5')-oligoadenylates is rapidly lost due to (i) cleavage of the 2'–5' internucleotide bond by a specific 2'–5'-phosphodiesterase which begins from the 2' end and degrades in a processive manner and (ii) one or several phosphatases which dephosphorylate (2'–5')A$_n$ to its core congener. This has led to the synthesis of a plethora of structurally modified (2'–5')A$_n$ analogs designed to improve cellular stability and uptake as well as better characterize its binding and activation of RNase L. For example, the half-life of (2'–5')A$_n$ in tissue culture is three hours; however the replacement of the 3' hydroxyl group of the adenosine moieties of (2'–5')A$_n$ by hydrogen atoms (i.e., cordycepin analogs) retains the properties of achirality and increases the half-life at the internucleotide linkages to seventeen hours against 2'-phosphodiesterase and cellular nuclease activity (Kariko, K.; Reichenbach, N. L.; Suhadolnik, R. J.; Charabula, R.; Pfleiderer, W. *Nucleosides & Nucleotides* 1987, 6, 497).

The (2'–5')oligo-3'-deoxyadenylates are nontoxic to cells and exhibit a broad spectrum of biological activities (Kariko, K.; Reichenbach, N. L.; Suhadolnik, R. J.; Charubala, R.; Pfleiderer, W. *Nucleosides & Nucleotides* 1987, 6, 497) (Torrence, P. F.; Imai, L.; Jamoulle, J. C.; Lesiak, K. *Chem. Scripta* 1986, 26, 191). Cordycepin trimer and its 5'-monophosphorylated analog fail to activate RNase L but do inhibit to some extent HIV-1 reverse transcriptase in vitro with no cell toxicity at a concentration of 62.5 μM (Sawai, H.; Imai, J.; Lesiak, K.; Johnston, M. I.; Torrence, P. F. *J. Biol. Chem.* 1983, 258, 1671). Furthermore, it appears unlikely that under experimental conditions, the cordycepin trimer serves as a prodrug of cordycepin which has no anti-HIV-1 activity in vitro (Montefiori, D. C.; Sobol, R. W.; Li, S. W.; Reichenbach, N. L.; Suhadolnik, R. J.; Charbula, R.; Pfleiderer, W.; Modliszewski, A.; Robinson, W. E.; Mitchell, W. M. *Proc. Natl. Acad. Sci. USA* 1989, 86, 7191).

Three adenosine monophosphate residues linked 2'–5' and a 5'-phosphorylated moiety are required for binding RNase L. For activation of RNase L, a 5'-di- or 5'-triphosphate is required (Kariko, K.; Reichenbach, N. L.; Suhadolnik, R. J.; Charubala, R.; Pfleiderer, W. *Nucleosides & Nucleotides* 1987, 6, 497). When the 2'14 5' phosphodiester bond(s) of a 2'–5'A trimer are replaced with 3'–5' phosphodiester linkages a $10^5$-fold decrease in inhibition of translation and a 13,000-fold decrease in ability to bind to RNase L are observed (Lesiak, K.; Imai, J.; Floyd-Smith, G.; Torrence, P. F. *J. Biol. Chem.* 1980, 258, 13082). There is no detectable 5'-rephosphorylation of the (2'–5')-3'-dA$_n$ core of trichloroacetic acid (TCA)-soluble cytoplasmic extracts of lymphocytes and lymphoblasts (Suhadolnik, R. J.; Doetsch, P. W.; Devash, Y.; Henderson, E. E.; Charubala, R.; Pfleiderer, W. *Nucleosides & Nucleotides* 1983, 2, 351).

It is unlikely that long nonphosphorylated (2'–5')-3'-dA$_n$ oligomers (n>4) will bind and activate RNase L or inhibit protein synthesis, (Lee, C.; Suhadolnik, R. J. *FEBS Lett.* 1983, 1, 205) however, they may have antimitogenic properties in intact cells (*Nucleosides & Nucleotides* 1983, 2, 351). Furthermore substitution of one the adenosine moieties of a (2'–5')A trimer with uridine results in a marked decrease in binding and activation of RNase L (Kitade, Y.; Alster, D. K.; Pabuccuoglu, A.; Torrence, P. F. *Bioorg. Chem.* 1991, 19, 283).

Based on these highly defined structural requirements the interaction of (2'–5')oligo-3'-deoxynucleotides with RNase L appears selective for adenosine residues of n<4 bases. Thus, it would not be expected that mixed base sequences of longer oligomers (≈21 mers), commonly used as modulators of gene expression, containing 3'-deoxy-(2'–5') internucleotide linkages would non-specifically inhibit protein synthesis by the (2'–5')A system.

In order for a 2'–5' oligonucleotide to serve as an effective analog to inhibit gene expression via an antisense or antigene strategy it must bind with complementary base sequences in the target nucleic acid. Theoretical studies on the stability of helices with 2'–5' linked nucleic acids have led to conflicting predictions (Anukanth, A.; Pannuswamy, P. K. *Biopolymers* 1986, 25, 729; Srinivasan, A. R.; Olson, W. K. *Nucleic Acids Res.* 1986, 14, 5461). Conformational analysis of dimer and trimer units of (2'–5')$A_n$, (n=2,3) by nuclear magnetic resonance and circular dichroism studies indicate that the 2'–5' nucleotides show a stronger tendency to base stack even at elevated temperatures than the corresponding 3'–5' ribonucleotides (Doornbos, J.; Den Hartog, J. A. J.; van Boom, J. H.; Altona, C. *Eur. J. Biochem.* 1981, 116, 403; Johnston, M. I.; Torrence, P. F. in *Interferons*, Volume 3, pp.189–298; Friedman, R. M., Ed.; Elsevier: Amsterdam, 1984; Torrence, P. F. in *Biological Response Modifiers—New Approaches to Disease Intervention*, pp.77–105; Torrence, P. F., Ed. Academic: New York, 1985; Lengyl, P. *Annu. Rev. Biochem.* 1982, 51, 251). Recently Turner has provided experimental evidence that complementary decamers of 2'–5' linked oligoribonucleotides can form antiparallel duplexes by Watson-Crick hydrogen bonding (Kierzek, R.; He, L.; Turner, D. H. *Nucleic Acids Res.* 1992, 20, 1685). The overall stability, however, of the 2'–5' duplexes is less than the corresponding 3'–5' duplexes, presumably due to a less favorable enthalpy change for association.

In the 3'-deoxynucleotide series, 2'–5' helices of mixed sequences and homopolymers also weakly strand associate as shown by Tm studies and a mobility shift assay (Dougherty, J. P.; Rizzo, C. J. Breslow, R. J. *Am. Chem. Soc.* 1992, 114, 6254). The association between complementary (2'–5') oligo-3'-deoxynucleotides was shown to improve when uridine was substituted for thymidine (Hashimoto, H.; Switzer, C. J. *Am. Chem. Soc.* 1992, 114, 6255). The complementary (2'–5')oligo-3'-deoxynucleotides $da_{12}$ and $dU_{12}$ exhibit a Tm of 22.8° C. versus 40.8° C. for the (3'–5')-linked DNA helix at high salt (Hashimoto, H.; Switzer, C. J. *Am. Chem. Soc.* 1992, 114, 6255).

The attractive features of conformational flexibility, high biological stability, low cell toxicity and the natural phosphodiester structure suggests that (2'–5')oligo-3'-deoxynucleotides represent a novel backbone structure to serve as an effective antisense inhibitor of gene expression in mammalian cells. An essential requirement in the antisense approach is that an oligonucleotide or its analog recognize and bind tightly to its complementary RNA sequence. The possibility of a 2'–5' oligomer associating with complementary 3'–5' nucleic acids has not been reported. It is the purpose of this invention to provide 2'–5' oligonucleotides for use in therapies for sequence specific inhibition of gene expression via hybridization to complementary mRNA or complementary duplex DNA.

Novel methodologies to evaluate large numbers of oligonucleotides with therapeutic value have recently been reported (Ellington, A. D.; Szostak, J. W. 1992, Nature, 355, 850) (Tuerk, C.; Gold, L. Science 1990, 249, 505) (Ellington, A. D.; Szostak, J. W. Nature, 1990, 346, 818). An experimental procedure called SELEX (systematic evolution of ligands by exponential enrichment) has been described as a general way to study protein-nucleic acid interactions (Tuerk, C.; Gold, L. Science 1990, 249, 505). In this procedure random pools of oligonucleotides containing approximately $10^{13}$ different molecular species, each having a different nucleotide sequence are synthesized. These pools are then incubated with the target molecule, and substances that bind with the highest affinity are isolated by physical separation techniques, such as affinity chromatography or filter binding. The isolated pool is then amplified by enzymatic procedures, and the binding, selection and amplification cycles are repeated until the pool is enriched with only those oligonucleotides that have the greatest affinity. This technique allows for the selection of oligonucleotides that, by chance, have the correct three-dimensional structure to bind to a target molecule. In subsequent steps, the high-affinity oligonucleotides are evaluated for their ability to inhibit activity, for example, enzymatic activity of the target to which they bind.

Aptamers having an affinity to large proteins or small organic target structures, can be selected. Thus, high-affinity inhibitors can potentially be found for any extracellular target molecule for which a therapeutic benefit may be derived. Most importantly, aptamer selection steps can be manipulated to screen the aptamer pool by more criteria than mere affinity for a given target molecule. Thus, other properties that are essential for therapeutic success can be conferred upon the final oligonucleotide.

BRIEF DESCRIPTION OF THE DRAWING

FIG. 1 is a graphic analysis of the effects of 3'deoxy-(2'–5') internucleotide linkage on duplex stability. Melting temperatures were determined by hypochromicity at 260 nm at temperatures from 10° C. to 70° C. x—x represents an equimolar mixture of (2'–5')-3'-d $A_g$ and poly U, o—o represents an equimolar mixture of (2'–5')-3'-d $A_g$ and poly dT.

SUMMARY OF THE INVENTION

In one aspect, the present invention provides a method of regulating gene expression in an organism which comprises hybridizing at least one 2'–5' oligonucleotide in a sequence specific manner to complementary mRNA or complementary duplex DNA of said organism. In a preferred embodiment, the 2'–5'0 oligonucleotide is from about 8 to about 75 nucleotides in length. In other preferred embodiments the 2'–5' oligonucleotide is a methylphosphonate, a phosphorothioate or, especially preferred, a phosphodiester. In yet other preferred embodiments, the 2'–5' oligonucleotide is chemically modified to increase its stability against nuclease degradation, to enhance its permeability into cells, to increase its binding strength upon hybridization, or to trigger a crosslinking reaction, cleavage reaction or combination thereof with complementary mRNA or complementary duplex DNA.

In another aspect of the invention, a method is provided for treating a disease characterized by undesired protein synthesis, which comprises administering to a human patient in need of such treatment at least one 2'–5' oligonucleotide having at least one nucleotide unit connected by a 2'–5' linkage wherein the oligonucleotide is substantially complementary to at least a portion of a sequence of an mRNA or duplex DNA encoding the undesired protein.

In a further aspect, a method is provided for treating an agricultural or horticultural disease characterized by undesired protein synthesis, which comprises administering to a plant in need of such treatment, at least one 2'–5' oligonucleotide having at least one nucleotide unit connected by a 2'–5' linkage wherein said oligonucleotide is substantially complementary to at least a portion of a sequence of an mRNA or duplex DNA encoding the undesired protein.

In yet another aspect, the invention provides a pharmaceutical composition which comprise a carrier and a therapeutically effective amount of at least one 2'–5' oligonucleotide having a nucleotide sequence substantially complementary to at least a portion of the mRNA transcript or duplex DNA encoding a target protein so as to block expression of the target protein.

In another aspect of the invention, there is provided a high affinity ligand that includes at least one 2'–5' oligonucleotide containing about 8 to 75 nucleotides wherein the ligand binds to DNA binding proteins. In a preferred embodiment, the ligand is capable of binding to a small molecule of molecular weight less than 5000.

For the purpose of this specification and appended claims, all references made herein to the term "2'14 5'" includes oligonucleotides formed from naturally occurring bases, sugars and phosphate linkages whereby the linkages between nucleotides occur from the 2' end of the sugar residue to the 5' end of the next sugar residue on the polynucleotide chain. In addition chimeric oligonucleotides containing a combination of 3'–5' and 2'–5' internucleotide linkages are also included.

Thus, the invention includes oligonucleotides of the formula (I):

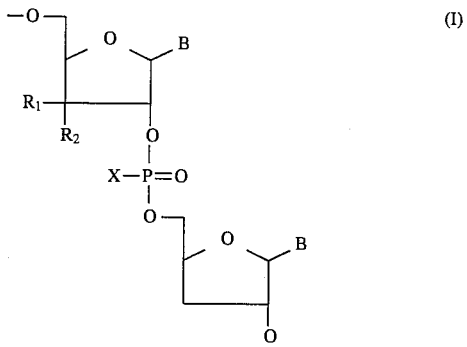 (I)

wherein B is a common nucleoside purine or pyrimidine base; $R_1$ and $R_2$ are independently nitrogen (azido), hydrogen, alkyl or alkyloxy of from 1 to about 20 carbon atoms, allyl or alkyloxy of from 2 to about 20 carbon atoms or aryl or aryloxy of from 6 to about 20 carbon atoms; and X represents an oxygen atom, a sulfur atom, alkyl, allyl, aryl, alkoxy, allyloxy, aryloxy, alkylamine, allylamine, arylamine, S-alkyl, S-allyl, or S-aryl.

"Dephospho" internucleotide analogs or nonphosphate internucleotide linkages wherein the bridging phosphate is replaced by a different group to connect or bridge nucleoside units, would include but are not necessarily limited to siloxane bridges, carbonate bridges, carboxymethyl ester bridges, acetamidate bridges, carbamate bridges or thioether bridges.

The term "substantially complementary38 is used herein to indicate that the oligonucleotide is capable of hybridizing to and forming a stable heteroduplex with its target sequence in the mRNA transcript in vivo.

The term "high affinity ligand" is used herein to refer to a ligand containing at least one oligonucleotide selected by affinity binding to a target molecule.

DETAILED DESCRIPTION OF THE INVENTION AND PREFERRED EMBODIMENTS

The present invention relates to pharmaceutical compositions containing nucleotides possessing 2'–5' internucleotide linkages; and the therapeutic use of such 2'–5' oligonucleotides. In accordance with one embodiment of this present invention, a 2'–5' oligonucleotide is hybridized to complementary nucleic acid which may be mRNA or duplex DNA for the purpose of modulating gene expression. The oligonucleotides of this invention may be represented by the following formula (I):

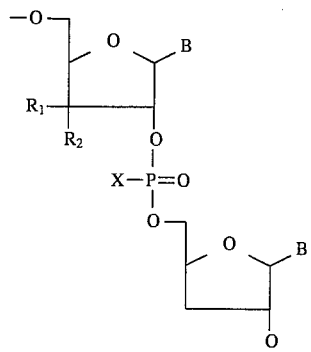

wherein B is a common nucleoside purine or pyrimidine base such as adenine, guanine, cytosine, thymine, uracil or a substituted purine or pyrimidine base. Such substituted bases include, but are not necessarily limited to 8-azidoadenine, 8-mercaptoadenine, 8-aminoadenine, 6-thioguanine, 8-azaguanine, 5-fluorouracil, and 5-methylcytosine. Natural sugars include β-D-ribofuranose and 3'-deoxy-β-D-ribofuranose. The glycosidic linkage in the oligonucleotide is in the naturally occurring β-anomeric form but also includes the α-anomeric configuration about the glycosidic bond. Oligonucleotides prepared from β-D-ribofuranose are linked from the 2' oxygen of the sugar to the 5' oxygen of the next nucleotide. The R1 and R2 groups at the 3' position of the β-D-ribofuranose are independently hydrogen, hydroxy, alkyl, allyl, aryl, alkoxy, allyloxy or aryloxy and may include from one to about twenty carbon atoms. The 3' position may also be an

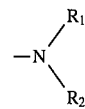

group wherein $R_1$ and $R_2$ are independently nitrogen (azido), hydrogen, alkyl, allyl or aryl groups containing from one to about twenty carbon atoms. The 2'–5' oligonucleotides may also include modified bases and sugars in part or all of the oligomer. Modified bases and sugars include but are not necessarily limited to derivatized bases, derivatized β-D-ribofuranosyl, 3'-deoxy-β-D-ribofuranosyl, 3'-deoxy-β-L-erythro-pentofuranosyl sugars and carbocyclic pentose sugars. X in formula (I) includes but is not necessarily limited to an oxygen atom (phosphodiester); sulfur atom (phosphorothioate); alkyl, allyl, or aryl of from one to about twenty carbon atoms (phosphonates); alkoxy, allyloxy, or aryloxy of from one to about twenty carbon atoms (phosphotriester); alkylamine, allylamine, or arylamine from one to about twenty carbon atoms (phosphoramidate); S-alkyl, S-allyl, or S-aryl of from one to about twenty carbon atoms (phosphorothioate). Other heteroatom substituents, e.g., N, O, S, may be attached to the carbon atom chains without departing from the spirit of the present invention. The methods used to prepare these derivatives are well known to those skilled in the art. The invention furthermore provides 2'–5' linked oligonucleotides containing substitution of either or both of the bridging 5' and 2' oxygen atoms of the phosphate backbone by different heteroatom(s) which include but are not limited to the examples listed in the table below wherein R is hydrogen, alkyl, allyl or an aryl group of from 1 to about twenty carbons. Examples of these types of substitutions are known for oligonucleotides containing 2'-deoxy-(3'–5') internucleotide linkages and may be used for oligodeoxynucleotides joined by 2'–5' linkages by similar chemical means apparent to those skilled in the art (see J. Goodchild *Bioconjugate Chem.* 1990, 1, 164 and references cited therein).

Modified Internucleoside Phosphates $$-A-\underset{D}{\underset{|}{\overset{B}{\overset{\|}{P}}}}-C-$$

| A | B | C | D |
|---|---|---|---|
| NH | O | O | O |
| O | O | NH | O |
| O | S | O | CH$_3$ |
| O | O | O | Se |
| O | O | S | O |
| O | NPr | O | NEt2 |
| O | S | O | NEt2 |
| O | Se | O | NEt2 |
| O | S | O | CH$_3$ |
| O | S | O | S |
| O | S | O | NHR |
| O | S | O | OPr |
| O | S | O | OEt |
| S | O | O | O |
| O | O | OPO$_3$ | O |
| CH$_2$ | O | O | O |
| S | O | O | O |
| S | S | O | O |
| O | O | S | CH$_3$ |

The 2'–5' oligonucleotide is not necessarily limited to linear single-stranded species but also includes oligomers containing secondary structures. Secondary structures may be regarded for the purposes of the present invention as a shape or conformation of the oligonucleotide that include, but are not limited to, circular, stem-loop, or "dumbbell-type" structures for the purpose of enhancing cellular uptake, nuclease resistance and/or improving binding. Secondary structure may be introduced by chemical or enzymatic methods well known in the art. Oligonucleotides transformed to these types of secondary structures may also include portions of nucleotides linked 3'–5'. A portion of the shape may include a sequence of (2'–5')oligo-3'-deoxynucleotides complementary to a target mRNA.

A preferred group of oligonucleotides useful in this invention are those wherein B is a natural base, especially adenine, guanine, cytosine, thymine and uracil; the sugar moiety is a natural sugar, especially β-D-ribofuranose and 3'-deoxy-β-D-ribofuranose; X is oxygen, sulfur, alkyl, especially methyl, alkoxy especially methoxy or ethoxy; and R1, and R2 are independently hydrogen, hydroxy, NH$_2$, or alkoxy, especially methoxy. Another preferred modification is sulfur substitution of both non-bridging oxygen atoms. An additional preferred group is substitution of the 5' and 2' bridging oxygen atoms independently by methylene or NH. Most preferably, the oligonucleotides are (2'–5')oligo-3'-deoxynucleotides comprising natural nucleosides and an oxygen phosphodiester backbone. More particularly, the (2'–5')oligo-3'-deoxynucleotides contain a natural phosphodiester backbone substantially complementary to a specific sequence of an mRNA, such that the oligonucleotide can specifically inhibit protein translation.

The cyanoethyl phosphoramidites may be obtained from the corresponding 3'-deoxynucleosides. There are many reported syntheses of 3'-deoxynucleosides including over twenty publications involving syntheses of cordycepin. However, a large number of these syntheses provide low to moderate yields due to poor transformations of the sugar moiety and formation of mixtures of 2' and 3'isomers. Robins has developed a three-step synthesis of cordycepin from readily available adenosine via the ribo-epoxide in 90% overall yield (Hanske, F.; Robins, M. J. *Tetrahedron Lett.* 1985, 26, 4295). The key feature in the synthesis is the regioselective ring opening of the ribo-epoxide, 2,3-anhydroadenosine by treatment with lithium triethylborohydride in 98% yield with no detectable amount of 2'-deoxyadenosine. The synthesis is efficient and may be applicable for the conversion of other commercially available ribonucleosides to 3'-deoxynucleosides. The 3'-deoxynucleosides can be efficiently converted to their fully protected analogs by known methods in the art. A preferred embodiment is acylation via the transient protection method of Jones and dimethoxytritylation of the 5'-hydroxyl to yield the desired protected 3'-deoxynucleoside (Ti, G. S.; Gaffney, B. L.; Jones, R. A. *J. Am. Chem. Soc.* 1982, 104, 1316).

A portion of the protected 3'-deoxynucleoside can be converted to its 2'-O-succinate and derivatized on lcaa-CPG via the 2' oxygen. In a preferred embodiment, 1-(3-dimethylamino propyl)-3-ethylcarbodiimide (DEC) is used for the conversion. (Pon, R. T,; Usman, N.; Ogilivie, K. K. *Biotechniques* 1988, 8, 768).

The corresponding cyanoethylphosphoramidite of protected 3'-deoxynucleoside can be prepared by known methods. Preferably, the protected nucleoside is condensed with 2-cyanoethyl N,N-diisopropylchlorophosphoramidite (Aldrich) in dichloromethane (25° C., 2 h) followed by aqueous work up and flash column chromatography purification (Sinha, N. D.; Biernat, J.; Köster, H. *Nucleic Acids Res.* 1984, 12, 4539).

The (2'–5')oligo-3'-deoxynucleotides for use in hybridizing to complementary RNA or complementary duplex DNA are 8–75 nucleotides in length and preferably 8–28 nucleotides in length and may contain different base sequences sufficient to define a unique sequence in the target mRNA transcript. At least 11–15 bases are needed to define a unique sequence in mRNA, where the lower figure refers to oligodeoxynucleotides containing only G and C and the higher figure is the length required for oligodeoxynucleotides containing only A and T (Marcus-Sekura, C. J. *Anal. Biochem.* 1988, 172, 289). Oligodeoxynucleotides of 15–20 bases are more often used since they form stable hybrids with melting temperatures well above 37° C. to ensure that antisense inhibition is elicited, assuming all other factors are favorably addressed. In a preferred embodiment of this invention, a 21 mer (2'–5')oligo-3'-deoxynucleotide is used. Specific oligomers containing a 3'-deoxy-(2'–5') internucleotide linkage may be complementary to regions of a viral DNA, viral RNA, mammalian DNA, or mammalian mRNA. The (2'–5')oligo-3'-deoxynucleotides may serve as therapeutic agents to inhibit synthesis of a specific protein or replication against specific complementary targets by an antisense or an antigene mechanism. The oligodeoxynucleotide may be a natural phosphodiester or a phosphate modified oligomer, e.g. phosphorothioate or methyl phosphonate.

The method of the present invention is effective against all prokaryotes and eukaryotes. Prokaryotes and eukaryotes which can serve as the target for the method of this invention include viruses, bacteria, mycoplasm, single celled eukaryotes, and animal and human cells. The present method can be used to modify cellular function of living cells in vitro (cell culture), or in vivo where cells form part of the tissue in an animal or human.

While preferred embodiments of the invention have been described herein, it will be evident to those skilled in the art from a reading of the present disclosure that oligodeoxynucleotides containing 2'–5' internucleotide linkages can be used. Modifications to or added substituents to the oligonucleotide directed to the phosphate backbone, 5' and/or 3' terminus, sugar moiety, nucleic acid bases to enhance or confer efficacious properties that would include but are not necessarily limited to solubility, cellular uptake, nuclease resistance, binding strength, a crosslink or cleavage event to irreversibly alter a complementary target are within the scope of the present invention. A complementary target strand may be mRNA or duplex DNA, where mRNA refers to mature RNA and nuclear pre-mRNA.

The stability of (2'–5')oligo-3'-deoxynucleotides of the present invention can be evaluated against the degradative effects of exonucleases and endonucleases by treatment with nucleases. The oligonucleotide is then analyzed by polyacrylamide gel electrophoresis (PAGE). The degradation products are quantitated by laser densitometry.

Various methods of formulation and administration of 2'–5' oligonucleotides are known to those skilled in the medical arts (Avis, K. in *Remington's Pharmaceutical Sciences*, pp.1518–1541; Gennaro, A. R., Ed.; Mack Publishing Company: Easton, Pa., 1985), the disclosures of which are incorporated herein in their entirety by reference thereto. Such methods of administration may include, but are not limited to, surface application, oral, or parenteral routes, injection into joints, subcutaneous injection, or via sustained release or other pharmaceutical methods of delivery depending on the disease state. Surface application of the compositions of the present invention includes topical application to such surfaces as skin, eyes, lungs, nares, ears, rectum, vagina, stomach, colon and the like.

Appropriate means for parenteral administration include 5% dextrose, normal saline, Ringer's solution and Ringer's lactate. The oligonucleotide may be stored as a lyophilized powder and reconstituted when needed by addition of an appropriate salt solution.

The oligonucleotide may be chemically modified so as to enhance its permeability into cells. Examples of receptor mediated endocytotic systems whereupon chemical conjugation to the oligonucleotide can be used to enhance cellular uptake by targeting a specific cell surface receptor include but are not limited to galactose, mannose, mannose-6-phosphate, transferrin, asialoglycoproteins, water soluble vitamins, e.g. transcobolamin (vitamin $B_{12}$), biotin, ascorbic acid, folates, any pharmacological agent or analog that mimics the binding of a water soluble vitamin, α-2 macroglobulins, insulin, epidermal growth factor, or attachment to an antibody against a surface protein of the target cell as in the case of the so-called immunotoxins. Chemical conjugation of the oligonucleotide may also include apolar substituents such as hydrocarbon chains or aromatic groups and polar substituents such as polyamines conjugated to further enhance intracellular uptake. Chemical conjugation of the oligonucleotide to an exogenous molecule may be achieved by covalent, ionic or hydrogen bonding either directly or indirectly by a linking group. Covalent bond formations between the oligonucleotide and an exogenous molecule is the preferred method for conjugation and can be performed via coupling techniques well known in the art.

Furthermore, transmembrane delivery of the oligonucleotide may be achieved by application of protein carriers, antibody carriers, liposomal or other vesicular delivery systems, lipofectin™, electroporation, direct cell fusion, viral carriers, osmotic shock and calcium-phosphate mediated transfection.

The (2'–5')oligo-3'-deoxynucleotides of the present invention hybridize to complementary RNA but not complementary single stranded DNA. The high level of RNA specificity and the strong binding of a (2'–5')oligo-3'-deoxynucleotide to RNA has not been previously reported, and represents a unique feature of this type of internucleotidic motif. Consequently, the (2'–5')oligo-3'-deoxynucleotides can be used to selectively inhibit gene expression by sequence specific hybridization to a target mRNA (antisense). Another possibility is that (2'–5')oligo-3'-deoxynucleotides may inhibit gene expression by binding to a complementary DNA duplex (antigene).

The (2'–5')oligo-3'-deoxynucleotides of the present invention may be prepared by solid phase or solution phase chemistries or enzymatic methods recognized by those skilled in the art. The most preferred method is solid-phase synthesis via cyanoethyl phosphoramidite methodology using standard reagents and protocols. The synthesis may be performed manually via the syringe technique, for example, or on an automated DNA synthesizer (e.g. Milligen 8600) (e.g. Tanaka, T.; Letsinger, R. L. *Nucleic Acids Res.* 1982, 10, 3249).

The following examples are provided to more fully illustrate the principles and practices of the invention. The examples are not intended in any way to limit the scope of the invention.

EXAMPLE 1

An octamer of (2'–5')-3'-deoxyadenylic acid was prepared via the syringe technique using standard phosphoramidite reagents and 3'-dA(bz) controlled pore glass (lcaa-CPG-500Å) solid support (0.2 μmol scale). The average coupling reaction yield was 98.0% as determined by absorbance of the dimethoxytrityl cation liberated on treatment with 3% dichloroacetic acid in methylene chloride. The oligodeoxynucleotide was cleaved from the solid support (concentrated ammonium hydroxide, 4 h, 25° C.) and the protecting groups were removed (concentrated $NH_4OH$, 5 h, 55° C.). The ammonium hydroxide was evaporated and the crude product purified by HPLC ion-exchange chromatography (Dionex Omni Pak™) and desalted on a μC18 Sep Pak™ cartridge (Millipore). An octamer of (2'–5')-3'-deoxyadenylic acid was prepared on a 3'-dA(Bz)-lcaa-CPG polymer support via the syringe technique (0.2 μmol scale) (Tanaka, T.; Letsinger, R. L. *Nucleic Acids Res.* 1982, 10, 3249) using standard solid-phase phosphoramidite reagents and protocols. Presently only 5'-DMT-3'-deoxyadenosine(bz) cyanoethyl phosphoramidite and 5'-DMT-3'-deoxyadenosine(bz)-long chain aminoalkyl controlled pore glass (lcaa-CPG-500Å) are commercially available.

EXAMPLE 2

To effectively inhibit gene expression in mammalian cells it is essential that an oligonucleotide recognize and bind tightly to its complementary sequence in the target nucleic acid. The affinity between two oligonucleotides can be determined by spectrophotometric methods, where absorbance versus temperature is measured for an equimolar mixture of complementary oligonucleotides (Wickstrom, E.; Tinoco, I. Jr. *Biopolmers* 1974, 13, 2367). Base stacking between complementary oligonucleotides is accompanied by a reduction in UV absorption (hypochromicity). When the temperature of the solution containing double-helical DNA (or RNA) is slowly raised, UV absorption increases suddenly at a certain temperature as the double helix dissociates. In this way it is possible to assess the hybrid stability from the melting temperature (Tm), or the temperature required for dissociation of half the duplex to single strand.

To assess the effects of the 3'-deoxy-(2'-5') internucleotide linkage on duplex stability the melting temperatures were determined by hypochromicity at 260 nm from 10° C. to 70° C. at a concentration of approximately 4 μM of each strand and compared with the natural (3'–5') oligomer. These results are shown in FIG. 1. When (2'–5')-3'-$dA_8$ was mixed with an equimolar concentration of poly U a monophasic helix-coil transition was observed upon heating the solution from 10° C. to 70° C. The Tm of (2'–5')-3'$dA_8$/ poly U heteroduplex in 10 mm sodium phosphate/pH 7.4 and 1.0 m NaCl was 53° C. compared to 54° C. for the natural 3'–5' linked $dA_8$/poly U heteroduplex. In control experiments, when (2'–5')-3'-$dA_8$ was mixed with poly C, poly A or alternating poly AU no hypochromicity was observed (data not shown). Furthermore, controls performed by Switzer (Hashimoto, H; Switzer, C. *J. Am. Chem. Soc.*, 1992, 114, 6255) where absorbance profiles versus temperature for pure (2'–5')-3'$dA_{12}$ separately, exhibit a slight linear change in hyperchromicity consistent with reported UV absorbance behavior of deoxyoligoadenylates (Leng, M; Felsenfeld, G. *J. Mol. Biol.* 1966, 15, 455). This is consistent with our own control experiments which showed no evidence of self-association when (2'–5')-3'$dA_8$ was heated along. Our control and experimental results taken together demonstrate no possibility of purimic self-association leading to the profile that results from the mixture of (2'–5')-3'$dA_8$ and poly U. It is particularly noteworthy that (2'–5')-3'-$dA_8$ exhibited a barely detectable variation in hyperchromicity with complementary poly dT when heated from 10° C. to 70° C. indicating that (2'–5')oligo-3'-deoxynucleotides do not bind to single strand DNA. In contrast, $dA_8$ exhibits apparent hypochromicity when mixed with complementary poly dT (Tm=62° C.), which is in agreement with reported values (Cassani, G. R.; Bollum, F. J. *Biochemistry* 1969, 8, 3928). In agreement with our findings, Breslow also observed that a (2'–5')oligo-3'-deoxynucleotide of a mixed adenine-thymine sequence fails to strand associate to a complementary (3'–5') linked oligodeoxynucleotide suggesting that this represents a general failure of oligos constructed with this unique internucleotide linkage (Dougherty, J. P.; Rizzo, C. J.; Breslow, R. *J. Am. Chem. Soc.* 1992, 114, 6254). The remarkable selectivity for hybridization of (2'–5')-3'-$dA_8$ to complementary RNA rather than to DNA suggests that (2'–5')-3'-$dA_8$ and related mixed base and longer oligomers may serve as a unique class of RNA-specific antisense oligodeoxynucleotides. Oligonucleotide analogs which show some selective binding to RNA complements have been reported (Adams, A. D.; Petrie, C. R.; Meyer, R. B. i *Nucleic Acids Res.* 1991, 19, 3647) (Durand, M.; Maurizot, J. C.; Thuong, N. T.; Hélène, C. *Nucleic Acids Res.* 1988, 16, 5039). The highest RNA selectivity occurs with enantio-DNA, since no hypochromicity was observed when L-$dA_6$ was mixed with poly dT (Fujimori, S.; Shudo, K.; Hashimoto, Y. *J. Am. Chem. Soc.* 1990, 112, 7436). However, the high preference of enantio DNA (L-$dA_6$) for complementary RNA also results in the formation of a much less stable heteroduplex (Tm=32.5° C.) relative to natural $dA_6$ (Tm= 5720 C.) in 10 mM Tris (pH 7.4)/10 mM $MgCl_2$.

What is claimed is:

1. A method of selectively hybridizing an oligonucleotide to RNA comprising hybridizing in a sequence specific manner at least one complementary oligonucleotide to said RNA, said oligonucleotide comprising at least one 2'-5' internucleotide linkage, wherein said oligonucleotide does not hybridize to complementary single stranded DNA in a sequence specific manner.

2. The method of claim 1 wherein said oligonucleotide is from about 16 to 25 nucleotides in length.

3. The method of claim 1 wherein said oligonucleotide is a methylphosphonate.

4. The method of claim 1 wherein said oligonucleotide has the formula

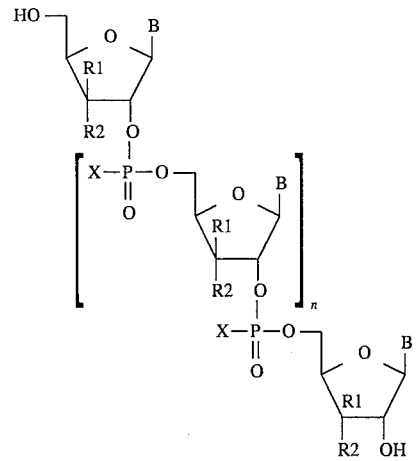

wherein B is selected from the group consisting of adenine, guanine, thymine, cytosine, 5-methylcytosine, uracil and inosine; $R_1$ and $R_2$ are each independently selected from the group consisting of hydrogen, hydroxyl, alkyl, aryl, alkoxy, alkyoxy, aryloxy, and azido; X is selected from the group consisting of oxygen, sulfur, aalkyl, allyl, aryl phosphonate having from 1 to about 20 carbon atoms, alkoxy, alloxy, aryloxy phosphotriester having from one to about 20 carbon atoms, alkylamine, allylamine, arylamine phosphoramidate having from one to about 20 carbon atoms, S-alkyl, S-allyl and S-aryl phosphorothioate having from one to about 20 carbon atoms; and n is an integer from 8 to 5.

5. The method of claim 1 wherein said oligonucleotide is a phosphorothioate.

6. The method of claim 1 wherein said oligonucleotide is a phosphodiester.

7. The method of claim 1 wherein said oligonucleotide is chemically modified at at least one site with ligands such as specific cell surface receptors, any pharmacological agent or analog to enhance its permeability into cells.

8. The method of claim 1 wherein said oligonucleotide is chemically modified at at least one site with reporter groups such as intercalators to increase binding strength of hybridization to complementary RNA.

9. The method of claim 1 wherein said oligonucleotide has a phosphate backbone and is substituted by $CH_2$, NH or S at at least one of the 5' or 2' oxygen atoms of the phosphate backbone, 10. The method of claim 4 wherein X=S, X=O or X=$CH_3$; and $R_1$ and $R_2$ are each independently selected from the group consisting of hydrogen, hydroxy, methoxy, allyloxy, azido and amino.

11. The method of claim 1 wherein said oligonucleotide is chemically modified at at least one site in sugar, base or backbone with a substituent that inhibits degradation without preventing hybridization with complementary RNA.

12. The method of claim 1 wherein said oligonucleotide is chemically modified at at least one site with a reporter group capable of triggering a cross-linking reaction or a cleavage reaction.

13. The method of claim 11 or 12 wherein the location of the chemical modification is the 5' terminus, the 2' terminus, a sugar moiety or a heterocyclic base of the oligonucleotide.

14. The method of claim 13 wherein the chemical modification comprises covalent bond formation between the oligonucleotide and one or more ligand molecules.

* * * * *